United States Patent
Hoffpauer et al.

(10) Patent No.: US 6,436,431 B1
(45) Date of Patent: Aug. 20, 2002

(54) FORTIFIED RICE BRAN FOOD PRODUCT AND METHOD FOR PROMOTING CARDIOVASCULAR HEALTH

(76) Inventors: Diane Wright Hoffpauer, P.O. Box 393, Crowley, LA (US) 70526; Salmon L. Wright, III, POB 1425, Crowley, LA (US) 70527

( * ) Notice: Subject to any disclaimer, the term of this patent is extended or adjusted under 35 U.S.C. 154(b) by 0 days.

(21) Appl. No.: 09/895,335

(22) Filed: Jul. 2, 2001

(51) Int. Cl.⁷ .................. A61K 35/78; A61K 31/51; A61K 31/375; A61K 31/4415; A61K 31/355; A61K 31/495; A61K 31/202; A23L 1/302

(52) U.S. Cl. .................................... 424/439

(58) Field of Search .................. 424/439, 442, 424/750; 514/52, 249, 276, 345, 458, 474, 558, 560, 824, 904; 426/72, 541, 543, 618, 623, 648, 807

(56) References Cited

U.S. PATENT DOCUMENTS

| | | | |
|---|---|---|---|
| 5,326,569 A | * 7/1994 | Acosta et al. | 424/440 |
| 5,545,414 A | * 8/1996 | Behr et al. | 424/484 |
| 5,612,074 A | * 3/1997 | Leach | 426/74 |
| 5,948,443 A | 9/1999 | Riley et al. | |
| 5,952,393 A | 9/1999 | Sorkin, Jr. | |
| 5,962,062 A | 10/1999 | Carrie et al. | |
| 6,126,943 A | 10/2000 | Cheruvanky et al. | |
| 6,180,660 B1 | 1/2001 | Whitney et al. | |
| 6,210,686 B1 | 4/2001 | Bell et al. | |

FOREIGN PATENT DOCUMENTS

| | | |
|---|---|---|
| EP | 0 699 437 | 6/1996 |
| WO | WO91/17670 | 11/1991 |

OTHER PUBLICATIONS

Marshall, W. E. and Wadsworth, J. J. (editors), Rice Science and Technology, Marcel Dekker, Inc., New York, pp. 384–389 (1994).

R. M. Saunders, "The Properties of Rice Bran as a Foodstuff," Cereal Foods World, pp. 632–636/Jul. 1990, vol. 35, No. 7.

Katherine Alaimo, Margaret A. McDowell, M.P.H., R.D., Ronette R. Briefel, Dr. P.H., R.D., Ann M. Bischof, R.D., Clifford R. Caughman, M.S., Catherine M. Lorla, M.S., M.A., and Clifford L. Johnson, M.S.P.H., Division of Health Examination Statistics, "Dietary Intake of Vitamins, Minerals, and Fiber of Persons Ages 2 Months and Over in the United States: Third National Health and Nutrition Examination Survey, Phase 1, 1988–91", Advanced Data pp. 1–28/No. 258, Nov. 14, 1994.

* cited by examiner

Primary Examiner—John Pak
(74) Attorney, Agent, or Firm—Michael Platt; Laura Donnelly; Patton Boggs, LLP

(57) ABSTRACT

A fortified rice bran food product for preventing and/or treating cardiovascular disease in animals, contains in admixture:

(a) rice bran as a carrier;
(b) at least about 12.5 milligrams of vitamin $B_1$ per 30 grams of the rice bran;
(c) at least about 250 milligrams of vitamin C per 30 grams of the rice bran;
(d) at least about 12.5 milligrams of vitamin $B_6$ per 30 grams of the rice bran;
(e) at least about 75 micrograms of vitamin $B_{12}$ per 30 grams of the rice bran;
(f) at least about 100 International Units of vitamin E per 30 grams of the rice bran;
(g) at least about 0.25 milligrams of folic acid per 30 grams of the rice bran; and
(h) at least about 250 milligrams of omega-3-fatty acids per 30 grams of the rice bran.

A method for preventing and/or treating cardiovascular disease in an animal involves orally administering a therapeutically effective amount of the fortified rice bran food product to the animal for a therapeutically effective period of time.

22 Claims, No Drawings

FORTIFIED RICE BRAN FOOD PRODUCT AND METHOD FOR PROMOTING CARDIOVASCULAR HEALTH

BACKGROUND OF THE INVENTION

This invention relates to a fortified food product which can be used as a dietary supplement or as an added ingredient for fortifying various food components. More particularly, this invention relates to a fortified rice bran food product that is capable of preventing and/or treating cardiovascular disease including, e.g., hypertension. In addition, this invention relates to a method of preventing and/or treating cardiovascular disease involving oral ingestion of the food product of this invention.

Cardiovascular disease is a major health issue in the United States. Several compositions and methods have been developed over the years in an attempt to prevent or treat this disease.

U.S. Pat. No. 6,126,943 (Cheruvanky et al.) discloses a method for reducing mammalian serum total cholesterol, LDL cholesterol, apolipoprotein B and triglyceride levels, by ingesting a stabilized rice bran derivative selected from the group consisting of an enzyme treated stabilized rice bran, an insolubilized fraction and mixtures thereof. The patent teaches that the rice bran used therein is rich in B-complex vitamins, vitamin E and its isomers, minerals like potassium, magnesium, and phosphorous, and several potent antioxidants.

U.S. Pat. No. 5,962,062 (Carrie, et al.) discloses a dietetically balanced milk product containing a lipid mixture based on a combination of milk fats and vegetable oils formulated so as to obtain an optimum balance of active substances in order to prevent unbalanced metabolic charges, in particular cardiovascular risks, and so that its organoleptic properties are close to those of milk. The lipid mixture may contain fatty acid oils such as EPA and DHA. The composition may also contain oils rich in vitamin E, oils rich in non-vitamin antioxidants (e.g., rice bran oil). The milk product may also be enriched with vitamins, e.g., E, A, D, C, $B_6$, $B_{12}$, folate and trace elements, e.g., iron, magnesium, and zinc.

U.S. Pat. No. 5,948,443 (Riley, et al.) discloses a total modular system of multivitamin and mineral supplementation composed of seven distinct modules for improving public health by insuring adequate intake of micronutrients needed for disease prevention and protection against nutritional losses and deficiencies. Module 4 contains aspirin or the like and is directed primarily for persons known to be at risk of coronary heart disease. The patent teaches that specific antioxidant micronutrients such as vitamins C, E, beta-carotene, selenium, copper, manganese, magnesium, folic acid, vitamin $B_6$, and vitamin $B_{12}$ enhance aspirin's ability to reduce risk of coronary heart disease.

WO 91/17670 discloses a foodstuff which is said to have prophylactic and/or curative effects and is suitable for use in the prevention and/or cure for diseases such as cardiovascular disease and cancer. The foodstuff is composed of at least one combination of at least polyunsaturated omega-3 fatty acid and/or its esters and one or more vitamins and pro-vitamins. The omega-3 fatty acid is preferably eicosapentaenoic acid (EPA) and/or docosahexaenoic acid (DHA) or their esters. The vitamin component is preferably made up of beta-carotene, vitamin C and vitamin E.

EP 0699437 discloses pharmaceutical preparations containing polyunsaturated fatty acids (e.g., EPA and DHA), their esters or salts, together with antioxidant vitamins or provitamins (e.g., vitamins E, A and C and carotenes, wherein the preparations are said to be useful in the prevention and/or treatment of atherosclerosis and of cardiovascular, nervous system, skin and malignant pathologies.

U.S. Pat. No. 6,210,686 (Bell et al.) discloses a dietary supplement and method for lowering risk of heart disease, wherein the supplement includes yeast fiber, folic acid or a salt thereof, vitamin $B_6$, vitamin $B_{12}$, and vitamin E. Optionally, the supplement may contain one or a combination of other vitamins (e.g., niacinamide, vitamin C), minerals, antioxidants, fibers and other dietary supplements (e.g., protein, amino acids, choline, lecithin, omega-3 fatty acids). The patent to Bell et al. teaches that, due to the presence of folate and vitamin $B_6$, the dietary supplement provides a second benefit of suppressing the level of homocysteine in the blood. The supplement provides a third benefit due to the presence of vitamin E which, according to the patent, preserves low density lipoproteins from oxidation.

U.S. Pat. No. 5,952,393 (Sorkin, Jr.) discloses a composition for reducing serum cholesterol in humans and animals, wherein the composition includes phytosterol and policosanol which together produce a synergistic effect in lowering serum cholesterol levels. The patent teaches that the policosanol used in the preferred embodiment of the invention is obtained from rice bran wax.

U.S. Pat. No. 6,180,660 (Whitney et al.) discloses a method for reducing or preventing the risk of first occurrence of a cardiovascular event in a subject having an average to mildly elevated level of LDL cholesterol and below average high-density lipoprotein ML) cholesterol, with no clinical evidence of coronary heart disease, comprising administering a prophylactically effective amount of a lipid altering agent such as a 3-hydroxy-3-methylglutaryl coenzyme A (HMG-CoA) reductase inhibitor alone or in combination with another lipid altering agent such as a fibrate, or niacin, to the subject. The active ingredients used in the method can be administered in oral forms such as tablets, capsules, pills, powders, granules, elixirs, tinctures, suspensions, syrups and emulsions.

Studies have shown that folic acid and vitamin $B_6$, taken in excess of recommended daily allowance, reduce the risk for developing heart disease by reducing levels of homocysteine. Homocysteine is associated with arterial occlusive disease.

Rice bran in and of itself has been considered for several years as an ingredient for food use because of the health benefits derived from its consumption. The bran as a by-product of rice milling has been used in the feed industry for many years, but with advanced techniques has only been recently considered as a food for human consumption. The nature of the bran is such that the remaining rice oils become rapidly oxidized so as to render it unacceptable for food. New and advanced techniques for stabilizing rice bran in the past ten years have altered its perception as an acceptable food grade product.

Several components of rice bran are desirable for the human diet. Rice bran protein has a high nutritional value that is highly digestible and is hypoallergenic. The proximate composition of stabilized, parboiled, defatted rice bran as stated in Saunders, R. M., "The Properties of Rice Bran as a Foodstuff", *Cereal Foods World,* 35:632 (1990), is as follows: moisture—6 to 9%, protein—23 to 27%; fat—0.5 to 1.5%, crude fiber—16 to 20%, and ash—11 to 14%. The fatty acid composition of the rice bran oil consists mainly of oleic, palmitic, and linoleic acids. In addition to the fatty acids, naturally occurring vitamins and minerals are present in varying amounts depending on growing conditions and milling methods. Vitamins and minerals present include vitamin A, thiamine, riboflavin, niacin, pyridoxine, panothenic acid, biotin, myoinositol, choline, para-aminobenzoic acid, folic acid, vitamin $B_{12}$, vitamin E, calcium, iron, magnesium, manganese, phosphorus, potassium and zinc. The major carbohydrates present are cellulose, hemicelluloses (pentosans), and starch. Beta-glucans are also present, forming part of the dietary fiber complex. Total dietary fiber content ranges from about 44% to about 51%, with the soluble fiber constituting from 2.4% to 2.9% of that total (see Marshall, W. E. and Wadsworth, J. J (editors), *Rice Science and Technology*, Marcel Dekker, Inc., New York, pp. 384–389 (1994)).

Due to the overall nutritional value of rice bran due to the high dietary fiber and low fat concentration, there has been considerable research in the last ten years on the use of rice bran in the diet for reducing the risk of cardiovascular disease. In a study reported in Gerhardt, A. L. and Gallo, N. B., "Effect of a Processed Medium Grain Rice Bran and Germ on Hypercholesterolemia", American Association of Cereal Chemists Meeting, Washington, D.C. (1989) (poster presentation), it was determined that rice bran was at least as effective in lowering cholesterol in male subjects as oat bran.

The American Heart Association (AHA) dietary guidelines for Americans has emphasized the importance of consuming a variety of fiber sources to obtain the different types of fibers found in foods. The AHA also states that fiber is important for gastrointestinal health as well as for cholesterol-lowering benefits. The AHA recommends a total dietary fiber intake of 25 to 30 grams from foods per day to maximize the cholesterol-lowering impact of a fat-modified diet. Current dietary fiber intakes among adults in the United States average about 15 grams or half the AHA-recommended intake of fiber per day (see Alaimo, K., McDowell, M., Briefel, R, Bischof, A, Caughman, C., Loria, C., and Johnson, C., "Dietary Intake: Vitamins, Minerals and Fiber of Persons Age Two Months and Over in the United States: Third National Health and Nutrition Examination Survey: Phase 1, 1988–91.,*Advance Data*. (1994) 258:1–28.

Other dietary ingredients have also been recommended by the scientific community for the treatment of cardiovascular disease. These ingredients include vitamin E, vitamin C, vitamin $B_6$, vitamin $B_{12}$, vitamin $B_1$, niacin, folic acid, and omega 3 fatty acids from fish oil.

Numerous studies have been conducted suggesting that the omega 3 fatty acids in fish oil, including eicosapentaenoic acid (EPA) and decosahexaenoic acid DHA), are beneficial to cardiovascular health. While not conclusive at this time, the studies have shown the lowering of LDL cholesterol levels and triglyceride levels. The mechanism is not clear as yet, but the results of an Italian study by GISSI-Prevenzione that included 11,000 blood clot patients who were studied for 2–3 years showed that a daily fish oil supplement containing 1 gram of omega 3 fatty acid reduced the death rate about 15% and reduced the risk of heart attacks by 50% (see *Berlingske Tidende* article, "Fish Can Save Heart Patients", week of 21/2000, Copenhagen, Denmark). Health organizations around the world, including the Food & Drug Administration (FDA), have recognized the possible benefit of omega-3-fatty acids from fish oil for the treatment of coronary heart disease (CHD). The concentrations recommended vary from organization to organization, but the range is from about 150 milligrams to about 2000 milligrams per day of omega-3-fatty acids.

Other nutrients that have been recommended for the treatment of cardiovascular disease also have ranges of recommended concentrations. In a survey of the literature, minimum levels for the nutrients are as follows: vitamin E—100 IU/day, vitamin C—250 mg/day, vitamin $B_6$—12.5 mg/day, vitamin $B_{12}$—75 mcg/day, vitamin $B_1$ —12.5 mg/day, niacin—25 mg/day, and folic acid— 0.25 mg/day. Four times the concentrations listed equals the optimal concentrations per day suggested for cardiovascular health (see Balch, J. F. and Balch, P. A., "Prescription for Nutritional Healing", Avery Publishing Group, Garden City Park, N.Y., page 6 (1997)).

In consideration of the possible health benefits in the treatment of coronary heart disease or in maintaining cardiovascular health with a diet high in fiber, low in fat, and adequate intakes of the nutrients vitamins $B_1$, $B_2$, $B_6$, $B_{12}$, C, E, niacin, folic acid, and omega-3-fatty acids from fish oil, a food product that contains all of those ingredients in specific concentrations would be of value to consumers.

While there are naturally occurring nutrients in rice bran such as vitamins $B_1$, $B_6$, $B_{12}$, and E, niacin, and folic acid, the concentrations vary depending on growth conditions of the rice and processing methods. Enzymes must be destroyed to prevent oxidation of the fat components of the rice bran and vitamins may also be destroyed in the process. Due to the variable concentrations of the natural vitamins, it would be desirable to fortify rice bran with these ingredients in controlled concentrations for treatment of cardiovascular disease. It would be further desirable to fortify rice bran with ingredients such as vitamin C and omega 3 fatty acids from fish oil that are not naturally present in rice bran, but would contribute significantly to the treatment of cardiovascular disease.

Therefore, a primary object of this invention is to provide a rice bran food product which has been fortified with controlled concentrations of cardiovascular-improving nutrients.

A further object of this invention is to provide a method for treating and/or preventing cardiovascular disease in animals, particularly humans, using a rice bran food product which has been fortified with controlled concentrations of cardiovascular-improving nutrients.

A still further object of this invention is to provide a food article composed of a rice bran food product which has been fortified with controlled concentrations of cardiovascular-improving nutrients.

These and other objects are achieved in the present invention.

SUMMARY OF THE INVENTION

The present invention provides a functional food product that is designed to prevent heart disease by providing nutrients which prevent and treat hypertension and coronary heart disease. The food product contains vitamins such as vitamins E, C, $B_6$, $B_{12}$, $B_1$, and niacin, folic acid (folate), and the omega-3-fatty acid(s) from fish oil, with rice bran as the carrier or base for the product. The properties of the rice bran also contribute to the cardiovascular health-providing benefits of the product because of the rice bran's inherent fiber and trace minerals. The food product contains the nutrients in quantities that promote a healthy cardiovascular system and that will prevent, and, in some cases, reverse the effects of coronary heart disease in progress.

Thus, one aspect of the present invention is directed to a fortified rice bran food product which is effective in preventing and/or treating cardiovascular disease and contains in admixture:

(a) rice bran as a carrier;

(b) at least about 12.5 milligrams of vitamin $B_1$ per 30 grams of the rice bran;

(c) at least about 250 milligrams of vitamin C per 30 grams of the rice bran;

(d) at least about 12.5 milligrams of vitamin $B_6$ per 30 grams of the rice bran;

(e) at least about 75 micrograms of vitamin $B_{12}$ per 30 grams of the rice bran;

(f) at least about 100 International Units of vitamin E per 30 grams of the rice bran;

(g) at least about 0.25 milligrams of folic acid per 30 grams of the rice bran; and (h) at least about 250 milligrams of omega-3-fatty acids per 30 grams of the rice bran.

The fortified rice bran of this invention is preferably in the form of a stabilized powder that is easily used as a dietary supplement or that can be added as an ingredient to a variety of foods to fortify the levels of the named nutrients in the food. Thus, a further aspect of this invention is directed to a food article containing the fortified rice bran food product.

The present invention also provides a method of preventing and/or treating cardiovascular disease in an animal, involving the step of orally administering a therapeutically effective amount of the food product of this invention to the animal for a therapeutically effective period of time.

DETAILED DESCRIPTION OF THE INVENTION

As stated above, one aspect of the present invention is directed to a fortified rice bran food product capable of preventing and/or treating cardiovascular disease. The food product of this invention contains:

(a) rice bran as a carrier;

(b) at least about 12.5 milligrams, preferably from about 12.5 milligrams to about 50 milligrams, of vitamin $B_1$ per 30 grams of the rice bran;

(c) at least about 250 milligrams, preferably from about 250 milligrams to about 1000 milligrams, of vitamin C per 30 grams of the rice bran;

(d) at least about 12.5 milligrams, preferably from about 12.5 milligrams to about 50 milligrams, of vitamin $B_6$ per 30 grams of the rice bran;

(e) at least about 75 micrograms, preferably from about 75 micrograms to about 300 micrograms, of vitamin $B_{12}$ per 30 grams of the rice bran;

(f) at least about 100 International Units (IU), preferably from about 100 to about 400 IU, of vitamin E per 30 grams of the rice bran (wherein 1 IU of vitamin E is equal to about 1 milligram of vitamin E);

(g) at least about 0.25 milligrams, preferably from about 0.25 milligrams to about 1.00 milligram, of folic acid (or folate) per 30 grams of the rice bran; and (h) at least about 250 milligrams, preferably from about 250 milligrams to about 1000 milligrams, of one or more omega-3-fatty acids per 30 grams of the rice bran.

In a preferred embodiment, the food product of this invention contains at least about 30 grams of the rice bran.

The omega-3-fatty acid(s) used as ingredient (h) in the food product of this invention may be EPA and/or DHA.

In addition to ingredients (a)–(h), the food product of this invention may contain one or more of other nutrients. Non-limiting examples of such nutrients include vitamin A, riboflavin, pantothenic acid, biotin, myoinositol, choline, para-aminobenzoic acid, calcium, iron, magnesium, manganese, phosphorus, potassium, zinc, carbohydrates (such as cellulose, hemicellulose and starch), beta-glucans, and one or more fatty acids (e.g., oleic, palmitic and/or linoleic acid).

The fortified rice bran food product of this invention is preferably prepared as follows. The first step involves mixing the nutrients (i.e., the vitamins $B_1$, $B_6$, $B_{12}$, C, E, niacin, folic acid and omega-3-fatty acids (from fish oil)) in the amounts recited above with the rice bran, using appropriate mixing equipment. The resulting mixture should be homogeneous and of even particle size. An approved food-grade antioxidant may be added at this point to prevent degradation of the materials before stabilization. A flow aid may also be added to make the materials easier to mix. The second step involves coating the materials with a food-grade coating such as cellulose, gums, sugars, or starch to seal the ingredients from oxygen and to stabilize them. The third step involves drying the mixture to a final moisture of from about 3% to about 5% by weight and homogenizing the particles. The fourth step should be an analytical assay to assure the minimum concentration of the required ingredients. The analysis may be performed by standard AOAC (Association of Official Agricultural Chemists) methods for grain or by specialized and validated solid phase extraction (SPE) and high pressure liquid chromatography HPLC) methods. In the case of specialized testing methods, extraction of the nutrients without destroying them is a critical step and requires methods not currently published by AOAC. An analysis of the crude and soluble fiber may, also be helpful for future studies on the fortified rice bran food product.

The food product of this invention may further contain one or more of flavors, coloring agents, spices and the like. Flavorings can be in the form of flavored extracts, volatile oils, chocolate flavorings, peanut butter flavoring, cookie crumbs, crisp rice, vanilla or any commercially available flavoring. Examples of suitable flavoring include but are not limited to pure anise extract, imitation banana extract, imitation cherry extract, chocolate extract, pure lemon extract, pure orange extract, pure peppermint extract, imitation pineapple extract, Imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil.

Emulsifiers may be added for stability of the final product. Examples of suitable emulsifiers include, but are not limited to, lecithin (e.g., from egg or soy), and/or mono- and di-glycerides.

Preservatives may also be added to the food product to extend product shelf life. Non-limiting examples of suitable preservatives include potassium sorbate, sodium sorbate, potassium benzoate, sodium benzoate, or calcium disodium EDTA.

The fortified rice bran food product of this invention is preferably in the form of a stabilized powder. As stated previously herein, the food product of this invention may be used as a dietary supplement or as an added ingredient to fortify food systems. Thus, another aspect of the present invention is directed to a food article comprising the fortified rice bran product of this invention. Non-limiting examples of food articles in which the food product of this invention may be used include beverages, snack bars, baked goods and puddings.

A further aspect of this invention is directed to a method for treating and/or preventing cardiovascular disease using the food product of this invention. The method involves orally administering a therapeutically effective amount of the food product to an animal, preferably a human, for a therapeutically effective period of time.

As used herein with respect to the amount of the food product administered to the animal, the term "therapeutically effective" means that amount of the product which will prevent and/or treat cardiovascular disease in the animal. With respect to the period of time in which the animal is administered the product, the term "therapeutically effective" means that period of time which is sufficient to prevent and/or treat cardiovascular disease in the animal.

The food product is preferably orally administered on a daily basis to the animal. In such instance, the food product is preferably administered in an amount of at least about 32 grams per day for a period of at least about 2 weeks. If the product is not administered on a daily basis, the amount and period of time will increase accordingly.

What is claimed is:

1. A fortified rice bran food product for treating and/or reducing the risk of cardiovascular disease in animals, comprising in admixture:
   (a) rice bran as a carrier;
   (b) at least about 12.5 milligrams of vitamin $B_1$ per 30 grams of the rice bran;
   (c) at least about 250 milligrams of vitamin C per 30 grams of the rice bran;
   (d) at least about 12.5 milligrams of vitamin $B_6$ per 30 grams of the rice bran;
   (e) at least about 75 micrograms of vitamin $B_{12}$ per 30 grams of the rice bran;
   (f) at least about 100 International Units of vitamin E per 30 grams of the rice bran;
   (g) at least about 0.25 milligrams of folic acid per 30 grams of the rice bran; and
   (h) at least about 250 milligrams of omega-3-fatty acids per 30 grams of the rice bran.

2. A product according to claim 1, containing from about 12.5 to about 50 milligrams of vitamin $B_1$ per 30 grams of the rice bran.

3. A product according to claim 1, containing from about 250 to about 1000 milligrams of vitamin C per 30 grams of the rice bran.

4. A product according to claim 1, containing from about 12.5 to about 50 milligrams of vitamin $B_6$ per 30 grams of the rice bran.

5. A product according to claim 1, containing from about 75 to about 300 micrograms of vitamin $B_{12}$ per 30 grams of the rice bran.

6. A product according to claim 1, containing from about 100 to about 400 International Units of vitamin E per 30 grams of the rice bran.

7. A product according to claim 1, containing from about 0.25 to about 1 milligram of folic acid per 30 grams of the rice bran.

8. A product according to claim 1, containing from about 250 to about 1000 milligrams of omega-3-fatty acids per 30 grams of the rice bran.

9. A product according to claim 1, containing at least about 30 grams of the rice bran.

10. A food article comprising the fortified rice bran food product of claim 1.

11. A method for treating and/or reducing the risk of cardiovascular disease in an animal, comprising
    (A) providing a fortified rice bran food product comprising in admixture:
        (a) rice bran as a carrier;
        (b) at least about 12.5 milligrams of vitamin $B_1$ per 30 grams of the rice bran;
        (c) at least about 250 milligrams of vitamin C per 30 grams of the rice bran;
        (d) at least about 12.5 milligrams of vitamin $B_6$ per 30 grams of the rice bran;
        (e) at least about 75 micrograms of vitamin $B_{12}$ per 30 grams of the rice bran;
        (f) at least about 100 International Units of vitamin E per 30 grams of the rice bran;
        (g) at least about 0.25 milligrams of folic acid per 30 grams of the rice bran; and
        (h) at least about 250 milligrams of omega-3-fatty acids per 30 grams of the rice bran; and
    (B) orally administering to the mammal for a therapeutically effective period of time a therapeutically effective amount of the fortified rice bran food product.

12. A method according to claim 11, wherein the product provided in step (A) contains from about 12.5 to about 50 milligrams of vitamin $B_1$ per 30 grams of the rice bran.

13. A method according to claim 11, wherein the product provided in step (A) contains from about 250 to about 1000 milligrams of vitamin C per 30 grams of the rice bran.

14. A method according to claim 11, wherein the product provided in step (A) contains from about 12.5 to about 50 milligrams of vitamin $B_6$ per 30 grams of the rice bran.

15. A method according to claim 11, wherein the product provided in step (A) contains from about 75 to about 300 micrograms of vitamin $B_{12}$ per 30 grams of the rice bran.

16. A method according to claim 11, wherein the product provided in step (A) contains from about 100 to about 400 International Units of vitamin E per 30 grams of the rice bran.

17. A method according to claim 11, wherein the product provided in step (A) contains from about 0.25 to about 1 milligram of folic acid per 30 grams of the rice bran.

18. A method according to claim 11, wherein the product provided in step (A) contains from about 250 to about 1000 milligrams of omega-3-fatty acids per 30 grams of the rice bran.

19. A method according to claim 11, wherein the product provided in step (A) contains at least about 30 grams of the rice bran.

20. A method according to claim 11, wherein the therapeutically effective amount of the product is at least about 32 grams.

21. A method according to claim 11, wherein the product is orally administered on a daily basis and the therapeutically effective period of time is at least about 2 weeks.

22. A method according to claim 11, wherein the animal is a human.

* * * * *